US010456434B2

(12) United States Patent
Dal Monte et al.

(10) Patent No.: US 10,456,434 B2
(45) Date of Patent: Oct. 29, 2019

(54) **EXTRACTS OBTAINED FROM CELL LINE CULTURES FROM PLANTS BELONGING TO THE OLEACEAE FAMILY (E.G. *SYRINGA VULGARIS*), THEIR PREPARATION AND USE**

(75) Inventors: Renzo Dal Monte, Creazzo (IT); Roberto Dal Toso, Creazzo (IT); Anacleto Minghetti, Milan (IT); Nicoletta Crespi Perellino, Milan (IT); Giovanna Pressi, Monteforte d'Alpone (IT)

(73) Assignee: CRODA ITALIANA S. P. A., Mortara, Pavia (IT)

(*) Notice: Subject to any disclaimer, the term of this patent is extended or adjusted under 35 U.S.C. 154(b) by 1672 days.

(21) Appl. No.: 12/780,275

(22) Filed: May 14, 2010

(65) Prior Publication Data

US 2011/0123646 A1 May 26, 2011

Related U.S. Application Data

(62) Division of application No. 11/455,501, filed on Jun. 19, 2006, now Pat. No. 7,718,199.

(30) Foreign Application Priority Data

Jun. 20, 2005 (EP) .................................. 05425442
Aug. 8, 2005 (EP) .................................. 05425586

(51) Int. Cl.
| | |
|---|---|
| *A61K 36/185* | (2006.01) |
| *A61K 8/60* | (2006.01) |
| *A61Q 7/00* | (2006.01) |
| *A61Q 11/00* | (2006.01) |
| *A61Q 19/00* | (2006.01) |
| *A61Q 19/02* | (2006.01) |
| *A61Q 19/08* | (2006.01) |
| *A61K 8/9789* | (2017.01) |

(52) U.S. Cl.
CPC ............ *A61K 36/185* (2013.01); *A61K 8/602* (2013.01); *A61K 8/9789* (2017.08); *A61Q 7/00* (2013.01); *A61Q 11/00* (2013.01); *A61Q 19/00* (2013.01); *A61Q 19/02* (2013.01); *A61Q 19/08* (2013.01); *A61K 2800/782* (2013.01)

(58) Field of Classification Search
None
See application file for complete search history.

(56) References Cited

U.S. PATENT DOCUMENTS

2004/0162246 A1 8/2004 Tu et al.
2005/0255541 A1 11/2005 Flachmann et al.

FOREIGN PATENT DOCUMENTS

JP 2005082522 A * 3/2005

OTHER PUBLICATIONS 2012, http://www.mayoclinic.com/health/hemophilia/DS00218/DSECTION=causes.*
Didry et al., Isolation and Antibacterial Activity of Phenylpropanoid Derivatives from Ballota Nigra, Journal of Ethnopharmacology, 1999, vol. 67, pp. 197-202, Elsevier Science Ireland Ltd.
Yajima et al., Protection of Cultured Rat Gastric Cells Against Oxidant Stress by Iron Chelation: Role of Lipid Peroxidation, Digestive Diseases and Sciences, Apr. 1995, vol. 40, No. 4, pp. 879-886, Plenum Publishing Corporation, New York, New York.
Toyokuni et al., Persistent Oxidative Stress in Cancer, Federation of European Biochemical Societies Letters, 1995, vol. 358, pp. 1-3, Federation of European Biochemical Societies.
Shi et al., Upregulated iNOS and Oxidative Damage to the Cochlear Stria Vascularis Due to Noise Stress, Brain Research, 2003, vol. 967, pp. 1-10, Elsevier Science B.V.
Organisciak et al., Susceptibility to Retinal Light Damage in Transgenic Rats with Rhodopsin Mutations, Investigative Ophthalmology & Visual Science, Feb. 2003, vol. 44, No. 2, pp. 486-492, Association for Research in Vision and Ophthalmology, Rockville, MD.
Lee et al., Microsatellite Instability and Suppressed DNA Repair Enzyme Expression in Rheumatoid Arthritis, The Journal of Immunology, 2002, pp. 2214-2220, The American Association of Immunologists, Inc., Bethesda, MD.
Fortoul et al., Nasal Cytology and Genotoxic Damage in Nasal Epithelium and Leukocytes: Asthmatics Versus Nonasthmatics, International Archives of Allergy and Immunology, 2003, vol. 130, pp. 232-235, S. Karger, Basel, Switzerland.
Greenspan et al., Oxidative Stress and Apoptosis in HIV Infection: A Role for Plant-Derived Metabolites with Synergistic Antioxidant Activity, Immunology Today, 1994, vol. 15, No. 5, pp. 208-213, Elsevier Science Ltd.
Tsukahara et al., Oxidative Stress and Altered Antioxidant Defenses in Children with Acute Exacerbation of Atopic Dermatitis, Life Sciences, 2003, vol. 72, pp. 2509-2516, Elsevier Science Inc.
Pinnell, Cutaneous Photodamage, Oxidative Stress, and Topical Antioxidant Protection, Journal of the American Academy of Dermatology, Jan. 2003, vol. 48, pp. 1-19, The American Academy of Dermatology, Inc.
Mittal et al., CD11b+ Cells are the Major Source of Oxidative Stress in UV Radiation-irradiated Skin: Possible Role in Photoaging and Photocarcinogenesis, Photochemistry and Photobiology, 2003, vol. 77, No. 3, pp. 259-264, American Society for Photobiology, Lawrence, KS.
Leonetti et al., Alpha-Tocopherol Protects Against Cisplatin-Induced Toxicity Without Interfering with Antitumor Efficacy, International Journal of Cancer, 2003, vol. 104, pp. 243-250, Wiley-Liss, Inc.

(Continued)

*Primary Examiner* — Terry A McKelvey
*Assistant Examiner* — Catheryne Chen
(74) *Attorney, Agent, or Firm* — Davis & Bujold PLLC; Michael J. Bujold

(57) ABSTRACT

The present invention refers to the use of extracts from selected and stabilized cell lines comprising phenylpropanoids with high anti-oxidant capacity having a verbascoside titer of between 20% and 90% and a chromophore-free fraction of between 80% and 10%, in human and veterinary medicine, and for nutritional and cosmetic purposes.

5 Claims, 1 Drawing Sheet

(56) References Cited

OTHER PUBLICATIONS

Clot et al., Monitoring Oxidative Damage in Patients with Liver Cirrhosis and Different Daily Alcohol Intake, Gut, 1994, vol. 35, pp. 1637-1643.
Yoshida et al., Weakened Cellular Scavenging Activity Against Oxidative Stress in Diabetes Mellitus: Regulation of Glutathione Synthesis and Efflux, Diabetologia, 1995, vol. 38, pp. 201-210, Springer-Verlag.
Mertens et al., Increased Low-Density Lipoprotein Oxidation and Impaired High-Density Lipoprotein Antioxidant Defense Are Associated With Increased Macrophage Homing and Atherosclerosis in Dyslipidemic Obese Mice: LCAT Gene Transfer Decreases Atherosclerosis, Circulation, Mar. 2003, vol. 107, pp. 1640-1646, The American Heart Association, Dallas, TX.
Bagchi et al., Molecular Mechanisms of Cardioprotection by a Novel Grape Seed Proanthocyanidin Extract, Mutation Research, 2003, vol. 523-524, pp. 87-97, Elsevier Science B.V.
Dib, Amyotrophic Lateral Sclerosis: Progress and Prospects for Treatment, Drugs, 2003, vol. 63, No. 3, pp. 289-310, Adis International Limited.
Olanow, A Radical Hypothesis for Neurodegeneration, Trends in Neurosciences, 1993, vol. 16, No. 11, pp. 439-443, Elsevier Science Publishers, Ltd., U.K.
Wang et al., Cytotoxic Effects of Mansonone E and F Isolated from Ulmus Pumila, Biological and Pharmaceutical Bulletin, 2004, vol. 27, No. 7, pp. 1025-1030, Pharmaceutical Society of Japan, Tokyo, Japan.
Niles et al., Resveratrol is a Potent Inducer of Apoptosis in Human Melanoma Cells, Cancer Letters, 2003, vol. 190, pp. 157-163, Elsevier Science Ireland Ltd.
Ochiai et al., Crocin Prevents the Death of Rat Pheochromyctoma (PC-12) Cells by its Antioxidant Effects Stronger than those of Alpha-Tocopherol, Neuroscience Letters, 2004, vol. 362, pp. 61-64, Elsevier Ireland, Ltd.
Echeverry et al., Cytoprotection by Neutral Fraction of Tannat Red Wine Against Oxidative Stress-Induced Cell Death, Journal of Agriculture and Food Chemistry, 2004, vol. 52, pp. 7395-7399, American Chemical Society.
Masamoto et al., Mushroom Tyrosinase Inhibitory Activity of Esculetin Isolated from Seeds of Euphorbia Lathyris L., Biosci. Biotechnol. Biochem., 2003, vol. 67, No. 3, pp. 631-634.
Kim et al., 4,4'Dihydroxybiphenyl as a New Potent Tyrosinase Inhibitor, Biological and Pharmaceutical Bulletin, 2005, vol. 28, No. 2, pp. 323-327, Pharmaceutical Society of Japan, Tokyo, Japan.
Thiboutot et al., Activity of the Type 1 5Alpha-Reductase Exhibits Regional Differences in Isolated Sebaceous Glands and Whole Skin, The Journal of Investigative Dermatology, Aug. 1995, vol. 105, No. 2, pp. 209-214, The Society for Investigative Dermatology, Inc., Cleveland, OH.
Bombardelli et al., Serenoa Repens (Bartram) J.K. Small, Fitoterapia, 1997, vol. 68, No. 2, pp. 99-113, Elsevier Inc.
Laakso et al., Determination of cis,cis-methylene Interrupted Polyunsaturated Fatty Acids in Aqueous Solutions by Lipooxygenase Chemiluminescence, Journal of Biochemical and Biophysical Methods, 1984, vol. 9, pp. 61-68, Elsevier Science Publishers B.V.
Lee et al., Protective Effect of Acteoside on Carbon Tetrachloride-Induced Hepatotoxicity, Life Sciences, 2004, vol. 74, pp. 1051-1064, Elsevier Inc.
Seidel et al., Phenylpropanoids from Ballota Nigra L. Inhibit in Vitro LDL Peroxidation, Phytotherapy Research, 2000, vol. 14, pp. 93-98, John Wiley & Sons, Ltd.
Buttke et al., Oxidative Stress as a Mediator of Apoptosis, Immunology Today, 1994, vol. 15, No. 1, pp. 7-10, Elsevier Science Ltd.
Korkina et al., Antioxidant and Chelating Properties of Flavonoids, Advances in Pharmacology, 1997, vol. 38, pp. 151-163, Academic Press, Inc.
Buege et al., Microsomal Lipid Peroxidation, Methods in Enzymology, 1978, vol. 52, pp. 302-310.
Ellis, Production of Hydroxyphenylethanol Glycosides in Suspension Cultures of Syringa Vulgaris, Phytochemistry, vol. 22, No. 9, pp. 1941-1943, 1983, Great Britain.
Lima et al., Antimicrobial Activity of a Mixture of Two Isometric Phenylpropanoid Glycosides from Arrabidaea harleyi A. H. Gentry (Bignoniaceae), Brazilian Journal of Pharmaceutical Sciences, vol. 39, No. 1, Jan./Mar. 2003, Brazil.

* cited by examiner

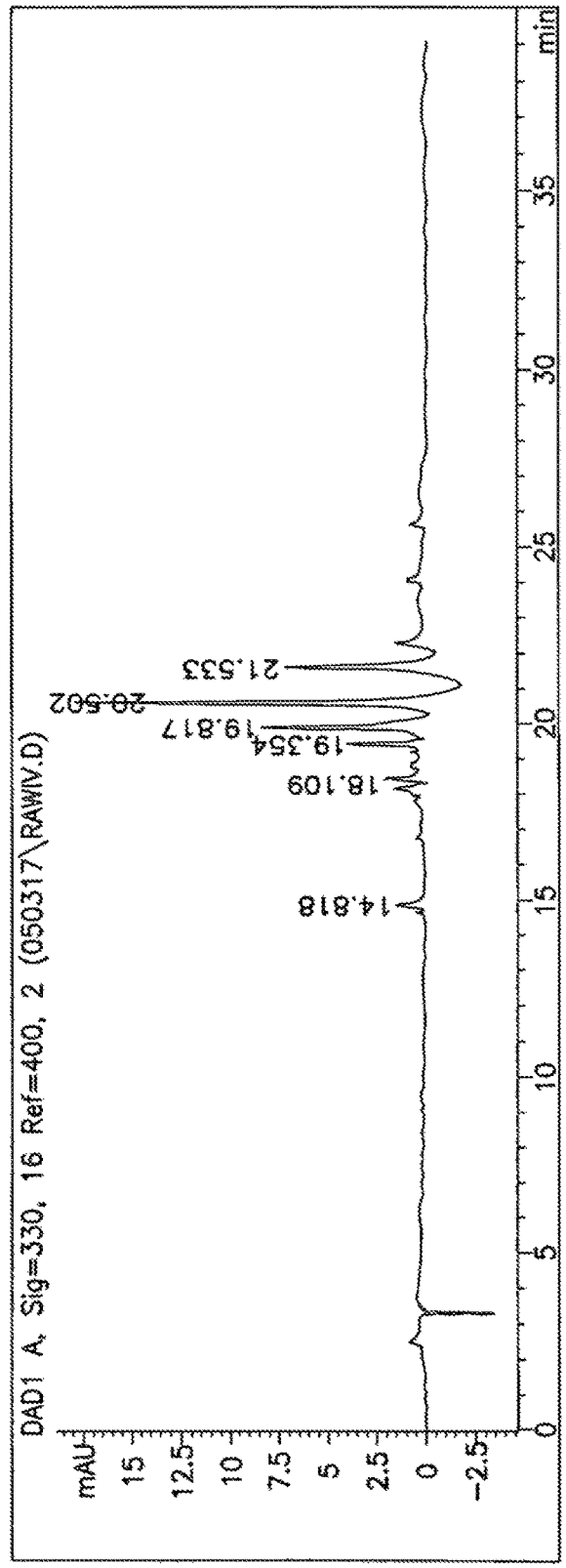

EXTRACTS OBTAINED FROM CELL LINE CULTURES FROM PLANTS BELONGING TO THE OLEACEAE FAMILY (E.G. *SYRINGA VULGARIS*), THEIR PREPARATION AND USE

This application is a division of application Ser. No. 11/455,501, filed Jun. 19, 2006.

FIELD OF THE INVENTION

The present invention refers to phenylpropanoid extracts titrated in verbascoside, the use thereof in human and veterinary medicine, for nutritional, and cosmetic purposes. Said extracts are derived from "in vitro" cell cultures from plants belonging to the Oleaceae family (e.g. *Syringa vulgaris*) obtained by fermentation. Furthermore, the present invention concerns the preparation and use of said extracts, for the production of drugs or nutritional or cosmetic substances, said extracts possessing not only antioxidant activity but also other important pharmacological properties.

BACKGROUND OF THE INVENTION

Numerous studies have confirmed that oxidative stress is a phenomenon which progresses over time, causing biological damage leading to cell death, and which is responsible for both the effects connected with lipoprotein peroxidation and death due to degeneration, in addition to death due to apoptosis. Indeed, oxidative stress has been recognised as a mediator of programmed cell death, responsible for the activation of T lymphocytes and the depletion of CD4+ T cells in AIDS (Buttke T. M., Sandstrom P. A. "Oxidative stress as a mediator of apoptosis" Immunology Today, 1994, 15(1): 7-10).

The antioxidant action of phenylpropanoids, and verbascoside in particular, has been amply described and is well known in the literature (Seidel et al. Phenylpropanoids from *Ballota nigra* L. inhibit in vitro LDL peroxidation. Phytother. Res., 2000, 14(2): 93-98; Chion et al. Acteoside protects endothelial cells against free radical-induced oxidative stress. J. Pharm. Pharmacol., 2004, 56(6): 743-8; Lee at al. Protective effect of acteoside on carbon tetrachloride induced hepatotoxicity. Life Sci., 2004, 74(8):1051-64), but suitable sources for the large scale production thereof are completely absent, due to the very low quantities typically present in plant tissues and the high costs associated with the purification process.

SUMMARY OF THE INVENTION

Hence, a first subject of the invention is a process for the production of extracts from plant cells belonging to the Oleaceae family (e.g. *Syringa vulgaris*) allowing the attainment of industrial quantities of phenylpropanoids.

A second subject of the invention relates to extracts of said plant cells for use in the preparation of drugs, nutritional or cosmetic substances.

Further subjects and the advantages of the present invention will become clearer from the following detailed description of the invention.

DETAILED DESCRIPTION OF THE INVENTION

The process of the invention comprises a first stage of cell culture selection based on the metabolite of interest.

Briefly, this process envisages the collection of plant tissue, the cleaning thereof, for example under running water, cutting into fragments of 2-5 cm and sterilisation on plates, for example by sequential treatment with 70% ethanol for approx. 15 minutes, 2% sodium hypochlorite for approx. 5 minutes and finally 0.05% $HgCl_2$ for approx. 1 minute. Between treatments, the plant fragments are washed, typically three or more times with sterile distilled water.

Each fragment of said tissue, chopped-up even further (explants), is placed on a Petri dish containing nutrient medium, solidified by the addition of Agar and supplemented with growth hormones without the addition of any antibiotics. The number of explants performed influences the outcome of the subsequent stages. Generally from 2000 to 5000 uncontaminated explants are sufficient to proceed to the subsequent selection stage.

Following a suitable period of time, undifferentiated callus tissue forms, which is then multiplied following transfer onto a greater surface area with fresh medium.

Furthermore, the plant cell line derived from the undifferentiated callus tissue is preferably stabilised by means of a certain number of transfers (sub-cultures) onto fresh culture medium. Particularly, it has been observed that in order to obtain a stable cell line, it is important to perform at least ten sub-cultures. Such medium is solid in nature, and may be advantageously constituted by 0.8-1% agar in a standard culture medium, to which has been added plant peptone, allowing a balanced supply of aminoacids and guaranteeing the maintenance of good cell wall integrity. Preferably, plant peptone will be added in quantities ranging between 500 and 4000 mg/l of culture medium.

A "stable cell line" is defined as a culture having the following characteristics:

high and constant proliferation rate over time;

preservation of the same phenotypic characteristics throughout various subcultures (cell colour, aggregate friability, size etc.);

constant secondary metabolite levels per unit of mass, over the course of the various subculture steps (secondary metabolite content is assessed by chemical analysis of the extracts);

constant primary metabolite content (protein, lipids and polysaccharides) per unit mass.

Subsequently, at the stabilisation stage, the cell line is subjected to "clonal selection". Such selection consists of growing the stabilised cells, for an appropriate amount of time (typically, 10-15 days of culture). Subsequently, individual cell aggregates are taken from the solid culture medium and each of said cell aggregates is inoculated into liquid culture medium described above.

Following fermentation for such time necessary to obtain adequate multiplication of the cell aggregate (hereinafter referred to as "clone"), a time generally comprised of between 10 and 15 days, the content of the metabolite of interest is determined for each clone.

Such operations may be repeated until a plant cell line clone is selected, in which production of the metabolite of interest is the highest.

It should be remembered that alternating periods of culture on solid and liquid media is essential for the clonal selection process of the present invention. Hence, it is essential that the clonal selection process described above does not conclude with the identification of the most active clone, but is constantly repeated so as to keep the selected clone phenotypically homogeneous.

The selected plant cell line is then multiplied in order to obtain a sufficient quantity of biomass to carry out the production fermentation stage. Said quantity will depend on the specific production requirements, the plant cell line typology used and the type of metabolite it is desired to produce.

The biomass thus obtained may be passed directly into the final fermenter, or can be subjected to one or more further growth stages in liquid medium, working with intermediate volumes.

Preferably, the process just illustrated includes the stages of:

a) cultivating a predetermined plant cell line, stabilised for a sufficient period of time to allow the multiplication of said cell line to give substantially distinct cell clusters, on solid medium;
b) removing said substantially distinct cell clusters from said solid medium and placing each of them in a separate liquid culture medium;
c) cultivating each of the said substantially distinct cell clusters in said liquid culture medium for a sufficient period of time to allow the multiplication of said cell clusters, and the analytical determination of the primary and/or secondary metabolites produced thereby;
d) performing a qualitative and quantitative determination of the primary and/or secondary metabolites produced by each of said cell clusters in said liquid culture medium;
e) selecting the cell cluster, capable of producing the greatest quantity of said metabolite of interest;
f) repeating the process cycle according to stages a), b), c), d) and e) on said cell cluster, selected according to stage e), a sufficient number of times until the quantity of said metabolite of interest produced by the selected cell cluster, and by the cell clusters deriving from further selection cycles, is essentially constant.

In addition, the subsequent fermentation may preferably consist of the following stages:
A) the inoculation of said plant clone into liquid medium, and the multiplication thereof for a sufficient period of time to obtain an increase in cellular mass of at least 300% of the weight thereof;
B) optionally, transfer of the suspension obtained from stage A) into fresh liquid culture medium and the multiplication thereof for a sufficient period of time to obtain an increase in cellular mass of at least 300% of the weight thereof;
C) optionally, the repetition of stage B) at least one additional time;
D) the transfer of the suspension obtained in stages A), B) or C) into fresh liquid culture medium in a fermenter to give a biomass, and conducting the fermentation under such conditions and for a sufficient period of time so as to obtain within said biomass, the production of said at least one metabolite of interest;
E) the separation of said at least one metabolite of interest from said biomass.

In accordance with one preferred embodiment, the fermentation will normally be performed at a temperature of between 15° C. and 35° C., typically around 25° C. and for a period of time normally between 7 and 42 days, preferably between 7 and 21 days. It is essential that the biomass be adequately aerated and that at the same time be kept stirred by means of stirring external to the fermenter. Indeed, it has been observed that plant biomass is comprised of cells having cell-walls that are poorly resistant to rupture. A stirrer submerged into the biomass acts mechanically on the cells and can easily cause the lysis thereof. However, it is necessary that the stirring, although delicate, be efficient, above all in the final fermentation stages when the biomass greatly increases in density. For the purposes of the present invention, particularly appropriate methods of stirring are orbital means of stirring. Such means of stirring preferably operate at 10-200 rpm, more preferably at around 120 rpm.

It is appropriate that the volume of the container (fermenter) in which the fermentation occurs be considerably greater than the volume of the biomass. Typically, the volume of the reactor will be from 50% to 200% greater than the biomass volume.

As already mentioned, efficient fermentation requires adequate oxygenation. Oxygenation is normally performed by using sterile air with a flow rate of 0.1-5 l/minute, more preferably 2-3 l/minute, for a volume of 10 liters of biomass. Alternatively, gas mixtures containing from 10% to 100% v/v of oxygen may be used.

As mentioned previously in relation to stirring, even oxygenation by means of over violent bubbling can cause rupturing of the cell walls. Hence it is necessary to ensure that oxygenation is performed delicately, for example by bubbling through appropriate diffusers. It will be preferable to use means of air or oxygen diffusion with nozzle delivery flow speeds comprised of between 10 m/min and 600 m/min, more preferably between 50 m/min and 350 m/min.

In addition, the shape of the fermentation chamber has significant importance. Indeed, it is recommended that it has a smooth and uniform surface, i.e. that there are no edges, corners or other parts which can cause the cell walls of the biomass rupture.

According to one particular embodiment of the present invention, additives increasing water oxygen solubility will be added to the biomass. Such additives will preferably be selected from those substances defined as "artificial blood", for example the perfluorinated hydrocarbons (PFC).

Particularly, as a non-limiting example of the invention, stabilised cell lines derived from *Syringa vulgaris* have been selected for their ability to produce phenylpropanoids (FP), and particularly verbascoside, in suitable qualitative and quantitative amounts.

Subsequently, said plant cell lines, selected in the aforesaid manner, have been extracted by means of the following procedure.

By way of non-limiting example, the details of a *Syringa vulgaris* cell line, the extraction conditions and an extract thereof, will now be described.

Morphological Characteristics of the Cell Line

The *Syringa vulgaris* cell line denominated IRB-SV25/B DSMZ (Deutsche Sammlung von Mikroorganismen und Zellkulturen, Braunschweig, D) accession N°: DSM 16857, accession date: 2004 September 15) has a clear hazelnut colouration and mucid (sticky) appearance.

Extraction Process

The extraction comprises the following stages in sequence:

a) subjecting the biomass, obtained in accordance with the selection process described previously, to an enzyme deactivation treatment;
b) homogenising the product obtained following step a);
c) separating the aqueous phase from the cell residues by means of gravity filtration, pressure filtration or centrifugation through a porous mesh, for example nylon, steel or cotton mesh etc., preferably having a porosity comprised of between 10 µm and 300 µm, more preferably between 50 µm and 150 µm;
d) performing an extraction of the aqueous phase obtained following step c) using hydrophobic interaction resin, preferably in batch;

e) recovering the absorbed substances (extract) from the resin by means of elution with ethanol, or a mixture of alcohols having up to 5 carbon atoms (preferably ethanol), in water in percentages varying from 30% up to just under 100% by volume.

According to one particular aspect of the invention, between steps a) and b) a biomass filtration step may be performed under the same conditions reported in step c), with the aim of recovering just the biomass itself without any fermenter culture medium.

In particular, cultures of the cell line IRB-SV25/B in suspension, obtained in accordance with the cited procedures, are harvested with ages comprised of between 7 and 21 days. The enzyme deactivation treatment occurs, for example, by means of thermal treatment. Particularly, said thermal treatment occurs by heating the biomass at a temperature comprised of between 50° C. and 150° C., preferably between 60° C. and 120° C., for a time of less than 5 minutes, so as to inactivate all enzymes. Preferably, the thermal treatment involves the use of steam. Subsequently, as described previously, the biomass is homogenised using an ultraturrax and then filtered or centrifuged. The substances present in the clear aqueous phase are batch extracted with hydrophobic interaction resin, preferably selected from polystyrene-divinylbenzene or acrylic matrix resins, and the absorbed products are recovered from the resin by means of one or more elution steps with aqueous ethanol, from 30% to 95% by volume.

In accordance with one particular embodiment, the entire biomass is filtered as described above, and subjected to thermal treatment with steam at 120° C. for a period of time varying between 5 and 30 minutes.

By the term "extract" is meant an extract obtained from cell cultures from plants belonging to the Oleaceae family (e.g. *Syringa vulgaris*), deriving from any of the extraction methods described below and comprising varying percentages of phenylpropanoids, such as for example verbascoside and isoverbascoside and a series of verbascoside analogues. Said "extract" further comprises a fraction, devoid of any characteristic chromophores, present in variable quantities depending on the preparation method and consisting mainly, but not exclusively, of oligo- and poly-saccharide, protein and lipid molecules.

The extracts contain phenylpropanoids of the following general formula (I)

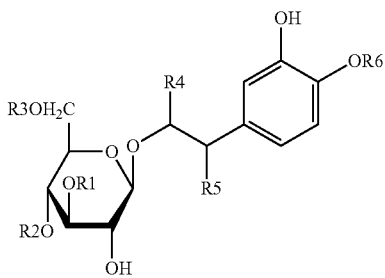

wherein:
R1 is a hydrogen atom or a monosaccharide with 5 or 6 carbon atoms and preferably rhamnose;
R2 is a hydrogen atom or is a caffeoyl (A) or feruloyl (B) group;
R3 is a hydrogen atom or a monosaccharide with 5 or 6 carbon atoms or a disaccharide with 10 to 12 carbon atoms or is a caffeoyl (A) or feruloyl (B) group;
R4 is a hydrogen atom or an alkyl group, preferably methyl, or a hydroxyl group;
R5 is a hydrogen atom or an alkyl group, preferably methyl, or a hydroxyl group, either free or condensed with, the alcohol group at position C2 of the monosaccharide group bound to it, in order to form a 1,4 dioxane ring;
R6 is a hydrogen atom or an alkyl group, preferably methyl;
when R3 is a caffeoyl (A) or feruloyl (B) group,

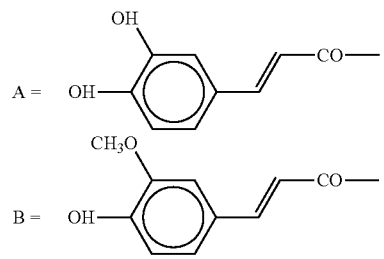

then R2 is always a hydrogen atom and vice versa.

The structures of verbascoside and isoverbascoside have been confirmed using mass spectrometry (MS) and nuclear magnetic resonance (NMR).

Verbascoside is a phenylpropanoid known also as acteoside, Kusaginin or Orobanchin (C. Jimenez et al. Nat. Prod Report 1994, 591-606) and is defined as b-(3,4-dihydroxyphenyl)-ethyl-O-α-L-ramnopyranosyl (1"-3')-b-D-(4'-O-caffeoil)-glucopyranoside. It is found along with isoverbascoside or b-(3,4-dihydroxyphenyl)-ethyl-O-α-L-ramnopyranosyl(1"-3')-b-D-(6'-O-caffeoil)glucopyranoside.

Hence, one of the aspects of the present invention consists in the fact that, by performing the extraction of the biomass obtained from the cell lines described above, extracts containing phenylpropanoids having general formula (I) are obtained.

Extraction occurs by bringing the clear solution obtained from treatment of the biomass into contact with an appropriate quantity of resin, separating the resin and eluting said resin with a suitable eluent.

Attainment of the extracts varies as a function of numerous parameters. The use of fermentation supernatant (which contains the part of the fraction devoid of chromophores and which is released from the cells during culture) during the filtration stage leads to a slight enrichment in phenylpropanoids due to the dilution effect. A second factor is the quantity of resin used in relation to the quantity of material to be extracted, with less resin promoting the selective attachment of phenylpropanoids and hence consequent enrichment of the eluate. Furthermore, different enrichments may be obtained depending on the EtOH/H$_2$O ratios used to recover the compounds absorbed onto the resin, since lesser percentages of ethanol in the eluent predominantly extract the fraction devoid of chromophore, while subsequent elution with a mixture containing a higher percentage of ethanol leads to the preferential extraction of phenylpropanoids.

Thus it is possible to obtain extracts containing from 20% to 90% phenylpropanoids by weight, preferably between 30% and 60%, with the remaining percentage fraction, comprised of between 80 and 10%, preferably between 70% and 40%, being comprised of a chromophore-free fraction, comprising mainly, but not exclusively, oligo- and polysaccharide, protein and lipid type molecules.

It has also been surprisingly discovered that the thermal treatment performed on the biomass causes the isomerisation of verbascoside to isoverbascoside, and that the extent of said isomerisation depends on the treatment temperature and time. Temperatures comprised of between 50° C. and 150° C., preferably between 60° C. and 120° C., for a period of time sufficient to cause isomerisation (measurable by HPLC analysis as reported previously), preferably between 5 and 34 minutes, are generally used to obtain the transformation of a percentage ranging between 40% and 60% of the verbascoside initially present into isoverbascoside. Hence the content of such substances in the filtered clear solution will also be modified. The thermal treatment may be performed by heating externally or internally for example by the insufflation of steam into the biomass.

Non-thermally treated biomass will generally contain a percentage of between 5% and 20% isoverbascoside with respect to the total mass of phenylpropanoids. Following thermal treatment, the percentage of isoverbascoside will generally be comprised of between 45% and 65% of the total mass of phenylpropanoids.

The above described isomerisation may occur in all those phenylpropanoids of general formula I wherein R3 is a hydrogen atom and R2 is anything other than hydrogen.

Hence, a process for the isomerisation phenylpropanoids of general formula I, wherein R3 is a hydrogen atom and R2 is anything other than hydrogen, comprising a thermal treatment stage of said phenylpropanoids as described above, constitutes a further subject of the present invention.

By way of non-limiting example, some embodiments of the extraction method are reported.

Example 1

Calluses grown on solid medium (GAMBORG B5 in 1% agar supplemented with 20 g/l sucrose, 2 g/l plant peptone, 1 mg/l kinetin, 1 mg/l naphthalenacetic acid, 0.2 mg/l indolacetic acid at pH 6.5) and subjected to subculture for at least three months, are inoculated into 20×300 ml flasks, each containing 50 ml of liquid medium (GAMBORG B5 supplemented with 20 g/l sucrose, 2 g/l plant peptone, 1 mg/l kinetin, 1 mg/l naphthalenacetic acid, 0.2 mg/l indolacetic acid at pH 6.5). Following fermentation for 7 days, the cultures are used to likewise inoculate 1000 ml flasks, each containing 250 ml of liquid medium which are then unloaded after a period 14 days. The biomass is combined and filtered through nylon mesh with a porosity of 100 μm. The cells are suspended in an equal volume of $H_2O$ and briefly treated with steam (3-4 minutes). The suspension is then homogenised using an ultraturrax and centrifuged in order to remove the sold residue. The latter is then taken up in 5 vol. of $H_2O$ then homogenised and centrifuged. The supernatants are combined and titrated by HPLC.

The analysis shows a total phenylpropanoid content, expressed as verbascoside, equal to the 12.3 g. To the aqueous solution is added 2 kg of Diaion HP 2MG resin, and the slurry left stirring overnight. After removal of the aqueous phase by filtration, the resin is washed with a first portion of 10 liters of hydroalcoholic mixture $EtOH:H_2O$ (20:80), then eluted with three 10 liter batches of $EtOH:H_2O$ mixture (80:20). The combined eluates are concentrated to a small volume in an evaporator, under reduced pressure. The lyophilised residual aqueous phase yields 10.3 g of a yellow powder. Typically, the extract thus obtained (Extract 1) has a titre equal to approx. 90% in phenylpropanoids expressed as verbascoside, and approx. 10%, in other components, constituted mainly, but not exclusively, by oligo- and polysaccharides, protein and lipid type molecules.

Example 2

40×1000 ml flasks, each containing 250 ml of culture obtained from calluses grown on solid medium (GAMBORG B5 in 1% agar supplemented with 20 g/l sucrose, 2 g/l plant peptone, 1 mg/l kinetin, 1 mg/l naphthalenacetic acid, 0.2 mg/l indolacetic acid at pH 6.5) following 15 days of fermentation are used to similarly inoculate 3 liter flasks, each containing 1 liter of liquid medium (GAMBORG 85 supplemented with 20 g/l sucrose, 2 g/l plant peptone, 1 mg/l kinetin, 1 mg/l naphthalenacetic acid, 0.2 mg/l indolacetic acid at pH 6.5). After a further 15 days of fermentation, these are in turn used to inoculate 10 30 liter fermenters, each containing 20 liters of liquid medium. After a further 15 days, the fermenters are in turn used as the inoculum, (equal to 200 liters) for a fermenter with a capacity of 1000 liters, containing 600 liters of medium. Fermentation is monitored by means of samples taken sequentially over time and, is terminated upon reaching an age of 20 days. Final production is equal to 3.1 g/l, for a total of 2,480 g of phenylpropanoids expressed verbascoside (600 liters+200 liters of inoculum). Steam at 120° C. is insufflated into the reactor for 20 minutes, then the biomass is unloaded therefrom, homogenised and centrifuged or filtered under the same conditions adopted for Example 1. To the clear aqueous phase is then added 150 kg of Diaion HP 2MG resin and this is then left stirring overnight. At the end of said period, the resin is allowed to settle into a column with a diameter of 50 cm and height of 150 cm. The spent aqueous phase is left to slowly flow out from the bottom of the column, which is then washed with copious amounts of water (50.0 liters), then firstly eluted with 200 liters of hydroalcoholic mixture $EtOH:H_2O$ (20:80), them with 500 liters of $EtOH:H_2O$ mixture (80:20), at a flow rate of 300 ml/min. The eluate is concentrated under, reduced pressure to give an aqueous residue which is then lyophilised 4,960 g of lyophilisate are obtained. Typically, extract thus obtained (Extract 2) is constituted by approx. 50% by weight of phenylpropanoids expressed as verbascoside, and approx. 50% of other components, constituted mainly, but not exclusively by oligo- and polysaccharides, protein and lipid type molecules.

Example 3

From HPLC analysis of the crude product obtained in example 2, verbascoside and its analogue isoverbascoside are the main components belonging to the class of caffeic derivatives, and are typically accompanied by at least six products belonging to the same class.

With the aim of purifying the compounds of interest, in order- to assess their activities, chromatographic purification using a 7×150 cm column, packed with Sephadex LH20 resin and equilibrated in 8% EtOH in water was, used. The column was loaded with 90 g of extract obtained from example 2 and eluted isocratically using the same solvent. All the fractions were analysed by HPLC using the method described below and those containing the same products combined, concentrated and lyophilised. In particular, two groups of fractions have been identified containing the pure molecules, verbascoside (27.1 g) and isoverbascoside (8.8 g).

High pressure liquid chromatography (HPLC) analysis is performed using a Phenomenex 4.6×150 mm C18 (2) column. Phase A—water/0.01 N phosphoric acid; Phase B—acetonitrile/0.01 N phosphoric acid; flow rate—0.8 ml/min. Gradient:

| Time | % B |
|------|-----|
| 0    | 0   |
| 10   | 10  |
| 15   | 20  |
| 20   | 25  |
| 25   | 35  |
| 30   | 45  |
| 35   | 55  |
| 40   | 0   |

The retention times of the 2 major phenylpropanoids present in the extracts are reported in table 1.

TABLE 1

Retention times of the phenylpropanoids verbascoside and isoverbascoside

| Phenylpropanoid: | verbascoside | isoverbascoside |
|------------------|--------------|-----------------|
| RT*              | 20.3-20.6    | 21.3-21.6       |

*Retention time in minutes (interval)

FIG. 1, enclosed herein, shows the chromatogram of an extract measured at 330 nm.

Table 2 (below) shows the percentage concentration of each component of Extract 1 and Extract 2 compared to the composition of purified verbascoside and isoverbascoside.

TABLE 2

| | Concentration % | | |
|---|---|---|---|
| Code | Verbascoside | FP | FS |
| Extract 1 | 82 ± 3 | 8 ± 2 | 10 ± 2.5 |
| Extract 2 | 35 ± 5 | 17 ± 3 | 48 ± 4 |
| Purified verbascoside | 99 | 1 | 0 |
| Purified isoverbascoside | 1 | 99 | 0 |

FP = fraction containing isoverbascoside and less abundant phenylpropanoids
FS = chromophore-free fraction In particular, it has been surprisingly observed that when an extract in accordance with the present invention is used, i.e. an extract also comprising the cromophore-free fraction, then the pharmacological activities are greater in comparison to the use of pure phenipropanoids.

In other cases, verbascoside and isoverbascoside have been found to exhibit pharmacological activities comparable to the inventive extracts. Particularly, the verbascoside and isoverbascoside have a platelet aggregation, anti-inflammatory and anti-lipoxygenase, anti-5alpha reductase, anti-tyrosinase, antifungal and metal-chelating ($Fe^{2+}$, $Fe^{3+}$, $Cu^{2+}$ e $Ni^{2+}$) activity.

In the following are reported some examples of the pharmacological action of the inventive extracts, verbascoside and isoverbascoside.

Example 4

Antioxidant Activities of the *Syringa Vulgaris* Extracts by Means of Biochemical Assays Based on Chemiluminescence Measurements

*Syringa vulgaris* Extracts 1 and 2, prepared as described in examples 1 and 2, have been used to assess in vitro antioxidant action with specific oxygen radical generating systems such as the superoxide anion ($O_2^-$), the hydroxyl radical (HO), the peroxynitrite radical ($ONOO^-$) and the inhibition of lipid peroxidation. The superoxide anion has been measured by a chemiluminescent assay based on the hypoxanthine (HPX)/xanthine oxidase (XOD) reaction using the Lumimax Superoxide Anion Detection Kit (Stratagene, La Jolla, Calif., USA) and following the manufacturer's instructions. Hydroxyl radical scavenger activity has been measured by means of the Fenton reaction for the production of hydroxyl radicals and chemiluminescent dosage (using a $Victor^3$ chemiluminometer, Wallac, Finland) with luminol. Peroxynitrite ions have been determined by means of dosage with a spontaneous generator of peroxynitrites (3-morpholinosidnonimine hydrochloride; SIN-1) and a stable reagent for the nitroxyl ions (2-(4-carboxyphenyl)-4,4,5,5-tetramethylimidazoline-1-oxyl-3-oxide potassium salt PTIO spin trap) then dosed by means of electron spin resonance (ESR) using a. Nippon Denshi JES-FR30. Lipid peroxidation has been generated using $Fe^{2+}$ induced-oxygen reactive species, and detected using thiobarbituric acid in accordance with Buege, J A & Aust, S D: Microsomal lipid peroxidation (Methods Enzymol. 1978, 52:302-310).

TABLE 3

The effects of *Syringa vulgaris* extracts on various assays of antioxidant activity (expressed as $IC_{50}$)

| | Superoxide radical | Hydroxyl radical | Peroxynitrite radical | Lipid peroxidation |
|---|---|---|---|---|
| Extract 1 | 0.20 µg/ml | 0.80 µg/ml | 1.7 µg/ml | 6.0 µg/ml |
| Extract 2 | 0.15 µg/ml | 0.61 µg/ml | 1.2 µg/ml | 5.8 µg/ml |
| Verbascoside | 3.1 µg/ml | 2.2 µg/ml | 1.6 µg/ml | 7.4 µg/ml |
| Rutin | 10 µg/ml | 3.9 µg/ml | 10 µg/ml | Not determined |
| Aloin | 7.6 µg/ml | 2.9 µg/ml | 12.3 µg/ml | Not determined |

Extract 1 and Extract 2 listed in Table are derived from *Syringa vulgaris* cell cultures. In said extracts, verbascoside is present at 0.82% and 35% by weight respectively. The results are expressed as the concentration inhibiting 50% of activity ($IC_{50}$). The values reported are the means of 6 independent assays.

In the assays, *Syringa vulgaris* extracts 1 and 2 have shown themselves to be extremely effective scavengers of oxygen free radicals, independently of their degree of purity. For the superoxide, hydroxyl and peroxynitrite radicals, both Extract 2, and Extract 2 possess greater capacity with respect to the classic flavonoids, such as for example rutin and aloin. In the superoxide and peroxynitrite generation assay, the $IC_{50}$ for rutin and aloin is 10 µg/ml and 7.6 µg/ml respectively, concentrations approximately 6 to 30 fold higher with respect to *Syringa vulgaris* Extract 1 and Extract 2 with verbascoside. The $IC_{50}$ for rutin and aloin for the inhibition of the production of hydroxyl radicals is 3.9 µg/ml and 2.9 µg/ml respectively, from 5 to 7 times higher with respect to the value determined for Extracts 1 and 2. Furthermore, the extracts have also shown themselves to be extremely effective in reducing iron ion-induced lipid peroxidation.

The antioxidant activity of pure verbascoside is surprisingly less effective in comparison to *Syringa vulgaris* Extracts 1 and 2 in activity assays against superoxide and hydroxyl radicals and, even though only slightly, in the inhibition of lipid peroxidase. This tends to indicate higher antioxidant activity in the extracts with respect to pure verbascoside.

Example 5

Anti-Inflammatory Activity of *Syringa Vulgaris* Extracts Verbascoside and Isoverbascoside on Whole Blood and White Blood Cells Anti-inflammatory activity has been assessed by measuring luminol dependent chemiluminescence generated by free radicals released from whole blood and from white blood cells. The assay has been performed using the following protocol: 10 µl of fresh human blood is mixed with 0.980 ml of Hanks saline solution containing $5 \times 10^{-5}$ M luminol and the test sample (at various concentrations). The chemiluminescent response is recorded continuously for 30 minutes at a temperature of 37° C. The results are expressed as $IC_{50}$ (mg/ml), i.e. as the minimum sample, concentration inhibiting chemiluminescence by 50% with respect to the control. To isolate white blood cells (WBC) from whole blood one proceeds in the following manner: 1 ml of fresh blood is layered onto a Hipaque gradient (p=1.119) and centrifuged at 250×g for 60 minutes at room temperature. Following centrifugation, the pellet containing the white blood cells is washed twice, using a large volume of cold Hanks saline solution. Finally, the washed WBCs are resuspended in 01 ml di HBSS containing foetal calf serum. $10^6$ WBC are added to a chemiluminometer cuvette. 10 µl of PMA (final concentration equal to 10 nM) are added to induce the formation of free radicals. The chemiluminescent response is recorded continuously for 30 minutes at a temperature of 37° C. The results are expressed as $IC_{50}$ (mg/ml), i.e. as the minimum sample concentration inhibiting chemiluminescence by 50% with respect to the control. The above assays have been performed on *Syringa vulgaris* Extracts 1 and 2, verbascoside and isoverbascoside.

Table 4 reports the values obtained for the above assays.

TABLE 4 anti-inflammatory activity of *Syringa vulgaris* extracts, verbascoside and isoverbascoside on whole blood and white blood cells.

|  | Whole blood chemiluminescence (IC 50 mg/ml) | White blood cell chemiluminescence (IC50 mg/ml) |
| --- | --- | --- |
| Extract 1 | 1.25 | 0.2 |
| Extract 2 | 0.18 | 0.14 |
| Verbascoside | 1.29 | 0.23 |
| Isoverbascoside | 1.30 | 0.25 |

The inhibition of the production of free radicals released by the white blood cells is correlated with the anti-inflammatory activity of the substance assayed. *Syringa vulgaris* Extracts 1 and 2, verbascoside and isoverbascoside show high inhibitory capacity in relation to the release of free radials from whole blood and stimulated white blood cells. Extract 2 has significantly higher activity with respect to Extract 1, verbascoside and isoverbascoside.

Example 6

The Platelet Anti-Aggregating and Disaggregating Activities of *Syringa Vulgaris* Extract 1, Verbascoside And Isoverbascoside Platelet enriched rabbit plasma has been used to assess the platelet anti-aggregating and disaggregating properties of *Syringa vulgaris* Extract 1, verbascoside and isoverbascoside. Platelet rich plasma has been obtained from rabbit venous blood by mixing it with a 3.8% sodium citrate solution (9:1 v/v). The solution has then been centrifuged at 460×g for 20 minutes. The supernatant has been collected and immediately used for the aggregation assays. Platelet aggregation has been recorded using a Chronolog "Ionised calcium platelet aggregometer" (Chrono-log Co., USA). All measurements have been performed at 37° C. with continuous stirring. One milliliter of the platelet suspension (in the presence or absence of the test substances) has been added to the cuvettes and incubated for five minutes to equilibrate the cells to 37° C. Then 10 µl of a solution of ADP (final concentration—10 µm) has been added and the luminous transmittance continuously recorded. The results are expressed as the DÒ/DÒÊ ratio, where DÒÊ and DÒ are the luminous transmittance values, in the absence and presence of extract respectively.

Platelet disaggregation (the disappearance of pre formed aggregates) has been determined using the same luminous transmittance curve 10 minutes following the addition of ADP. The results are expressed as the DR/DRk ratio, where DRk and DR, are the luminous transmittance in the absence and presence of extract. The test substances, diluted in physiological solution (isotonic saline) (pH 7.4) are pre-incubated with the platelet rich plasma (1:10 v/v) for 5-40 minutes. The aggregation measurements have then been performed. Physiological solution carrier has been added to the control samples (1:10 v/v). The values are reported in Table 5.

TABLE 5

The effect of Extract 1, verbascoside and isoverbascoside on ADP induced platelet aggregation-disaggregation

| Extract 1 (mg/ml) | Aggregation (% with respect to control) | Disaggregation (% with respect to control) |
| --- | --- | --- |
| 0.001 | 100 ± 5* | 85 ± 15 |
| 0.01 | 93 ± 11 | 113 ± 13 |
| 0.1 | 88 ± 10 | 138 ± 18 |
| 1.0 | 26 ± 5# | 75 ± 25 |
| Verbascoside (mg/ml) 1.0 | 24 ± 6# | 73 ± 21 |
| Isoverbascoside (mg/mL) 1.0 | 25 ± 6# | 75 ± 21 |

*Mean ± SD (n = 6);
p < 0.001 vs. control

Extract 1, verbascoside and isoverbascoside cause a significant reduction in platelet aggregation at concentration of 1 mg/ml, whilst no significant effects on platelet disaggregation are evident.

Example 7

The Fe2+, Fe3+, Cu2+ and Ni2+ Metal Chelating Action of *Syringa Vulgaris* Extracts, Verbascoside and Isoverbascoside The chelating activities of *Syringa vulgaris* extracts, verbascoside and isoverbascoside in relation to $Fe^{2+}$, $Fe^{3+}$, $Cu^{2+}$ and $Ni^{2+}$ metal ions has been determined by means of spectrophotometric measurements using a Shimadzu 1770 UV spectrophotometer. The activities of chelating agents depends on the association constant (equilibrium) of their reactions with the metals according to the following reaction [1]:

$$Me + n \text{ chelator} \overset{K_{eq}}{\rightleftharpoons} Me(\text{chelator})_n \quad [1]$$

wherein $K_{eq}$ is the equilibrium constant equal to the ratio of concentrations at equilibrium of a complex and product of equilibrium concentrations of metal ions and a chelator:

$$K_{eq} = \frac{[Me(\text{chelator})_n]}{[Me][\text{chelator}]^n} \quad [2]$$

The method used for determining chelating activity is well documented in the literature (Korkina L G, Afarras'er IB. Antioxidant and chelating properties of flavonoids. Adv. Pharmacol., 1997, 38:151-63). The results are expressed as Keg ($M^{-1}$) calculated for a pure phenylpropanoid. This way the chelating activity against ferrous (Fe II), ferric (Fe III), copper (Cu II) and nickel ions has been calculated.

reductase, type I and type II) produced by genetically modified yeast. Enzyme activities have been determined in the presence of *Syringa vulgaris* and *Serenoa repens* extracts, verbascoside isoverbascoside.

Type I 5 alpha reductase activity has been assayed by incubating the enzyme in 0.1M Tris-citrate buffer (pH 7.0), containing 5 μM ($^{14}$C) radio-labelled testosterone (Amersham, Sweden) and 5 mM NADPH (Sigma) in a final volume of 5 ml. The solution thus obtained has been incubated for 1 hour at 37° C.

Determination of the type II 5 alpha reductase activity has been performed in an analogous manner to that just described, with the exception of a different pH value for the 0.1 M Tris-citrate buffer (pH 5.0).

In both assays, the steroids have been extracted using 5 ml of methylene chloride. The extracts have then been dried under a stream of nitrogen and the dried residues obtained have, been dissolved in 20 μl of a chloroform-methanol mixture (2:1 v/v). An aliquot of said mixture has been deposited on the surface of a silica gel TLC plate. The

TABLE 6

Chelation equilibrium constants (Keq, $M^{-1}$) for the *Syringa vulgaris* extracts, verbascoside and isoverbascoside.

| Samples | $Fe^{2+}$ (Keq, $M^{-1}$) | $Fe^{3+}$ (Keq, $M^{-1}$) | $Cu^{2+}$ (Keq, $M^{-1}$) | $Ni^{2+}$ (Keq, $M^{-1}$) |
|---|---|---|---|---|
| Extract 1 | $0.47 \times 10^6 \pm 0.14 \times 10^6$ | $0.14 \times 10^6 \pm 0.04 \times 10^6$ | $0.12 \times 10^6 \pm 0.03 \times 10^6$ | $1553 \pm 499$ |
| Extract 2 | $1.90 \times 10^6 \pm 0.14 \times 10^6$ | $0.13 \times 10^6 \pm 0.04 \times 10^6$ | $0.11 \times 10^6 \pm 0.03 \times 10^6$ | $1704 \pm 387$ |
| Verbascoside | $0.45 \times 10^6 \pm 0.11 \times 10^6$ | $0.12 \times 10^6 \pm 0.05 \times 10^6$ | $0.12 \times 10^6 \pm 0.04 \times 10^6$ | $1427 \pm 319$ |
| Isoverbascoside | $0.46 \times 10^6 \pm 0.12 \times 10^6$ | $0.13 \times 10^6 \pm 0.04 \times 10^6$ | $0.13 \times 10^6 \pm 0.06 \times 10^6$ | $1398 \pm 362$ |
| Rutin | $0.14 \times 10^6 \pm 0.04 \times 10^6$ | $0.16 \times 10^6 \pm 0.04 \times 10^6$ | $0.11 \times 10^6 \pm 0.04 \times 10^6$ | $635 \pm 169$ |

The chelating activities of *Syringa vulgaris* Extracts 1 and 2, verbascoside and isoverbascoside in relation to $Fe^{2+}$ and $Ni^{2+}$ metal ions, are higher with respect to that of rutin.

Example 8

Anti 5 Alpha Reductase and Anti-Lipoxygenase Activities of the *Syringa Vulgaris* Extracts, Verbascoside and Isoverbascoside, Useful for the Treatment of Juvenile Acne and the of Hair Loss Juvenile acne shows a multifactorial aetiology; one factor which plays a fundamental role is the following: during puberty and adolescence, there is increased production of the hormone testosterone. In the skin, this hormone is converted by the enzyme 5 alpha reductase into the hormone dihydrotestosterone, the latter; causes enlargement of the sebaceous glands with a concomitant increase in sebum secretion. High levels of the enzyme 5 alpha reductase is also one of the major causes of hair loss (Thiboutot D., Harris G., Iles V., Cimis G., Gillilaud K., Hagari S. Activity of the type 1,5 alpha reductase exhibits regional differences in isolated, sebaceous glands and whole skin. J. Invest. Dermatol. 1995; 105:209-14).

Data reported in the bibliography, show that extracts derived from the plant *Serenoa repens*, have anti-hair loss activity in that they possess inhibitory activities in relation to two enzymes: 5-alpha reductase, and lipoxygenase (*Serenoa repens* (Bartram) J. K. Small. Fitoterapia 1997; LXVIII (2):99-113).

Determination of the 5 alpha reductase inhibitory activities by *Syringa vulgaris* extracts, verbascoside and isoverbascoside in comparison to *Serenoa repens* extracts. Said determination, has been performed using enzymes (5 alpha solvent mixture used to develop the TLC has been the sane used to solubilise the dried residues. At the end of the TLC run, following UV detection, the $R_f$ values of the metabolites have been compared with, those of standard steroids, chromatographed simultaneously with the other samples. For quantification of the results, the spots have been scraped from the TLC plate and extracted with 2 ml of ethyl acetate. The extracts obtained have been analysed, using scintillation fluid, with the aid of a Wallach a-counter. The enzyme activity has been calculated from the percentage conversion (C %) of the substrate into final product:

C %=[counted product/(counted substrate+product)]×100. The results are reported in the following Table 7. Determination of the inhibition of lipoxygenase activity The inhibition of lipoxygenase activity by *Syringa vulgaris* extracts, verbascoside and isoverbascoside has been demonstrated using a method based on the measurement of chemiluminescence (Laakso S., Lilius E M, and Turunen P. Determination of cis-,cis-methylene interrupted polyunsaturated fatty acids in aqueous solutions by lipoxygenase chemiluminescence. J. Biochem. Biophys. Methods 1984; 9(1):61-68).

The results obtained are summarised in table 7.

TABLE 7

Inhibition of the enzymes 5 alpha reductase and lipoxygenase (expressed as $IC_{50}$) by *Syringa vulgaris* extracts, verbascoside and isoverbascoside, and *Serenoa repens* plant extracts.

| Samples assayed | Type I 5 alpha reductase inhibition (IC50) | Type II 5 alpha reductase inhibition (IC50) | Lipoxygenase inhibition (IC50) |
|---|---|---|---|
| Extract 1 | 12 μg/ml | 19 μg/ml | 11 μg/ml |
| Extract 2 | 9.2 μg/ml | 12.3 μg/ml | 10.5 μg/ml |
| Verbascoside | 13 μg/ml | 21 μg/ml | 12 μg/ml |

TABLE 7-continued

Inhibition of the enzymes 5 alpha reductase and lipoxygenase (expressed as IC$_{50}$) by *Syringa vulgaris* extracts, verbascoside and isoverbascoside, and *Serenoa repens* plant extracts.

| Samples assayed | Type I 5 alpha reductase inhibition (IC50) | Type II 5 alpha reductase inhibition (IC50) | Lipoxygenase inhibition (IC50) |
|---|---|---|---|
| Isoverbascoside | 12 µg/ml | 20 µg/ml | 11.5 µg/ml |
| *Serenoa repens* extract | 12 µg/ml | 44 µg/ml | 18.5 µg/ml |

*Syringa vulgaris* Extracts 1 and 2, verbascoside and isoverbascoside have significant inhibitory capacity in relation to the enzymes 5 alpha reductase (type I and type II) and lipoxygenase. The inhibitory activity of the *Syringa vulgaris* extracts, verbascoside and isoverbascoside is greater than that shown by *Serenoa repens* plant extracts, particularly in relation to type II 5-alpha reductase, which is the principal agent responsible for the onset of acne and androgenetic alopecia (male pattern baldness).

Example 9

Anti-Tyrosinase Activity of the *Syringa Vulgaris* Extracts, Verbascoside and Isoverbascoside to be Used for Skin Bleaching The enzyme tyrosinase catalyses the reactions leading to melanin biosynthesis from tyrosine. L-tyrosine is oxidised to 3,4 dihydroxyphenylalanine (L-DOPA), through the action of the enzyme tyrosinase, and again by means of a reaction catalysed by the same enzyme, 3,4 dihydroxyphenylalanine is converted to DOPAquinone. Substances inhibiting tyrosinase activity produce clearing/bleaching effect on the skin, since they block melanin synthesis. The method used to determine the inhibition of tyrosinase activity in the oxidation reaction of L-tyrosine to L-DOPA is that described in Kim et al. (4,4'-Dihydroxybiphenyl as a new potent tyrosinase inhibitor. Biol. Pharm. Bull. 28(2), 323-327, 2005). The method applied for determination of the inhibition of tyrosinase activity in the conversion of L-DOPA to DOPAquinone is that described in Masamoto et al. (Mushroom tyrosinase inhibitory activity of esculetin isolated from seeds of *Euphorbia lathyris* L. Biosci. Biotechnol. Biochem., 67(3), 631-634, 2003). The results obtained from the inhibition assay of tyrosinase activity by *Syringa vulgaris* total extracts, verbascoside and isoverbascoside in comparison to resorcinol and kojic acid, are summarised in tables 8 and 9.

TABLE 8

Percentage tyrosinase enzyme activity inhibition in the oxidation of L-tyrosine to L-DOPA, by *Syringa vulgaris* extracts, verbascoside and isoverbascoside in comparison to resorcinol and kojic acid.

| Compound | concentration | Test L-tyrosine-DOPA inhibitory activity (%) |
|---|---|---|
| Resorcinol | 250 µg/ml | 56.9 |
| Kojic acid | 250 µg/ml | 94.1 |
| Extract 1 | 250 µg/ml | 29 |
| Extract 2 | 250 µg/ml | 31.3 |
| Verbascoside | 250 µg/ml | 19.6 |
| Isoverbascoside | 250 µg/ml | 10.9 |

As may be observed from the data summarised in table 8, *Syringa vulgaris* Extracts 1 and 2, verbascoside and isoverbascoside display inhibitory activity towards the enzyme tyrosinase.

TABLE 9

Percentage tyrosinase enzyme activity inhibition in the conversion of L-DOPA to L-DOPAquinone, by *Syringa vulgaris* extracts, verbascoside and isoverbascoside in comparison to resorcinol and kojic acid.

| Compound | concentration | Test LDOPA-DOPAquinone inhibitory activity (%) |
|---|---|---|
| Resorcinol | 100 µg/ml | 0 |
| Kojic acid | 100 µg/ml | 35 |
| Extract 1 | 100 µg/ml | 40.4 |
| Extract 2 | 100 µg/ml | 35.4 |
| Verbascoside | 100 µg/ml | 20.6 |
| Isoverbascoside | 100 µg/ml | 10 |

Table 9 highlights the high inhibitory capacity of Extracts 1 and 2, verbascoside and isoverbascoside towards the enzyme tyrosinase. The enzyme inhibitory activities of the *Syringa vulgaris* extracts 1 and 2 are higher with respect to those of the reference molecules resorcinol and kojic acid.

Example 10

Oxidative Stress on Human Pulmonary Endothelial Cell (A549) Cultures

In the following example, reference is made to certain substances, herein reported using the corresponding abbreviations:

| BSO | buthionine [S,R] sulphoximine |
| GSH | reduced glutathione |
| DCF | Dichlorofluorescein |
| DCF-DA | Dichlorofluorescein diacetate |
| FCS | foetal calf serum |
| MTT | 3-(4,5-dimethylthiazol)-2,5-diphenyl tetrazol bromide |
| ROS | Reactive Oxygen Species |

$10 \times 10^5$ A549 cells (ATCC-CCL195) have been seeded into wells with 3 ml of DMEM/medium (HAM'S F12K) with 10% FCS and incubated at 37° C. in a 5% $CO_2$, water vapour saturated atmosphere. After 24 hours the culture medium is replaced by medium supplemented with 5.55 mM galactose, which is left in contact with the cells for 20 hours. The medium is once again replaced with medium containing galactose in the presence or absence of the test compound. After 5 hours, quantitative measurement of the ROSs is performed by washing the cells with phosphate buffer and then incubating them with 30 µM DCF-DA in buffer solution. At the end of a 15 minute incubation, excess DCF-DA is removed from the cells by washing, prior to measuring the fluorescence emitted.

Parameters

Fluorimetry.

Antioxidant activity measurements are performed using a (Hitachi F3010) spectrophotometer with excitation at 488 nm and measuring emission at 525 nm, and values are expressed in pmoles, by extrapolation from the calibration curve constructed using known quantities of DCF, in relation to total cellular protein. Values are thus expressed in % ages with respect to the ROS, content of the cells not subjected to oxidative stress, to which are assigned a value of 100.

Sample Preparation

*Syringa vulgaris* Extracts 1 and 2 and ascorbic acid have been dissolved in phosphate buffer.

Results

Extracts 1 and 2 significantly reduce ROS concentrations in a dose-dependent manner and are more potent than ascorbic acid, as demonstrated in Table 10.

TABLE 10

The antioxidant effect of *Syringa vulgaris* Extracts 1 and 2

| Treatment | Concentration | % ROS in picomoles |
| --- | --- | --- |
| Oxidative stress | | 100.02 ± 3.11 |
| Extract 1 | 20 mM | 67.74 ± 3.81* |
| Extract 1 | 30 mM | 57.21 ± 2.77* |
| Extract 2 | 20 mM | 65.83 ± 5.68* |
| Extract 2 | 30 mM | 57.23 ± 2.31* |
| Ascorbic acid | 1 mM | 62.91 ± 3.82* |
| Verbascoside | 20 mM | 85 ± 7* |

Mean ± SD (n = 6);
*p > 0.05 vs. BSO. Student- Newman- Keuls test

In the different percentage proportions of verbascoside, Extracts 1 and 2 show overlapping biological activities, markedly superior to ascorbic acid without displaying any peroxidising activity, frequently encountered with low concentrations (<100 µM) of ascorbic acid. Furthermore, the biological activity is unexpectedly greater than pure verbascoside.

Example 11

The Protective Effect of *Syringa Vulgaris* Extracts Against Oxidative Stress in PC12 Cells This assay has the aim of determining the protective capacity, of *Syringa vulgaris* extracts, in relation to oxidative stress induced cell death in rat pheochromocytoma cell cultures (PC12 cell line).

The assay has been performed as described in the literature (Echevery C. et al. Cytoprotection by neutral fraction of tannat red wine against oxidative stress-induced cell death. J. Agric. Food Chem., 2004, 52(24): 7395-9. Ochiai T. et al. Crocin prevents the death of rat pheo-chromycitoma (PC12) cells by its antioxidant effects stronger than those of alpha-tocopherol. Neurosci. Lett., 2004, 362(1):61-4).

The results obtained are summarised in table 11, and are expressed as the ratio between the numbers of viable cells after 72 hours in the samples with respect to control.

TABLE 11

Increase in PC12 viability with respect to control.

| Sample | Concentration | Ratio of viable treated cells over control |
| --- | --- | --- |
| Control | 0 µg/ml | 1 |
| Extract 1 | 100 µg/ml | 10 |
| Extract 1 | 500 µg/ml | 30 |
| Extract 1 | 1000 µg/ml | 35 |
| Extract 2 | 100 µg/ml | 15 |
| Extract 2 | 500 µg/ml | 25 |
| Extract 2 | 1000 µg/ml | 37 |
| Isoverbascoside | 100 µg/ml | 4 |
| Isoverbascoside | 500 µg/ml | 10 |
| Isoverbascoside | 1000 µg/ml | 10 |

The results obtained indicate that *Syringa vulgaris* Extracts 1 and 2 display higher protective activity and survival in relation to oxidative stress in PC12 cells, since the quantity of viable cells after a 72 hour assay is up to 37 fold higher than the viable cells in the control. This activity, is much more evident with Extracts 1 and 2 in comparison to pure isoverbascoside.

Example 12

Antiproliferative Activity of *Syringa Vulgaris* Extracts

The antiproliferative activity of the *Syringa vulgaris* extracts has been assayed, using an in vitro mode, envisaging the use of a stabilised human melanoma cell line (A375). The above cell lines, provided by the American Type Culture Collection, Rockville, Md. (USA), have been maintained in culture at 37° C. and 5% $CO_2$, in a defined nutrient medium (Dulbecco's Modified Eagle's Medium (MEM) supplemented with 10% foetal calf serum (FCS). The *Syringa vulgaris* extracts have been diluted in culture medium, so as to obtain the minimum possible dilution at which no toxic effects are observed. Each extract diluted in medium has been sterilised by filtration (using 0.2 µm filters). The assay consists of two experimental stages: A cytotoxicity test and, an antiproliferative test. Such assays have been performed as described in the literature (Niles, R M et al. Resveratrol is a potent inducer of apoptosis in human melanoma cells. Cancer Lett., 2003, 190(2): 157-63; Wong D. et al. Cytotoxic effects of mansone E and F isolated from *Ulmus pumula*. Biol. Pharm. Bull., 2004, 27(7): 1025-30).

The data obtained from the above assay are summarised in tables 12 and 13.

TABLE 12 cytotoxic and antiproliferative activities of *Syringa vulgaris* Extract 1 on A375 melanoma cells

| | | conc ug/mL Extract 1 | | | | | IC5 |
| --- | --- | --- | --- | --- | --- | --- | --- |
| | h | 1 | 1 | 5 | 10 | 50 | 100 | ug/m |
| citotox | 24 | 0 | 0 | 0 | 0 | 0 | 0 | |
| | 48 | 0 | 0 | 0 | 0 | 0 | 0 | |
| | 72 | 0 | 0 | 0 | 0 | 0 | 80% | |
| antiprolif | 24 | 0 | −10% | 0 | 0 | −25% | −75% | 529 |
| | 48 | 0 | 0 | 0 | 0 | −65% | −90% | 366 |
| | 72 | −8% | −15% | −10% | −15% | −70% | −90% | 200 |

TABLE 13 cytotoxic and antiproliferative activities of

| | | conc ug/mL Extract 2 | | | | | IC5 |
| --- | --- | --- | --- | --- | --- | --- | --- |
| | h | 1 | 10 | 50 | 10 | 50 | 100 | ug/m |
| citotox | 24 | 0 | 0 | 0 | 0 | 0 | 0 | |
| | 48 | 0 | 0 | 0 | 0 | 0 | 0 | |
| | 72 | 0 | 0 | 0 | 0 | 0 | 30% | |
| antiprolif | 24 | 0 | 0 | 0 | 0% | −30% | −70% | 515 |
| | 48 | 0 | 0 | 0 | 0% | −50% | −90% | 493 |
| | 72 | 0 | −5% | −15% | −25% | −70% | −95% | 220 |

*Syringa vulgaris* Extract 2 on A375 Melanoma Cells

The results obtained indicate that *Syringa vulgaris* Extracts 1 and 2 display a significant anti-proliferative effect towards A375 melanoma cells.

Example 13

Antimycotic Activity of *Syringa Vulgaris* Extracts, Verbascoside and Isoverbascoside Towards Strains of *Malassezia Furfur* and *Tricophyton Rubrum*

*Tricophyton rubrum* and *Malassezia furfur* are fungal microorganisms responsible for giving rise to a number of skin diseases. Particularly, *Malassezia furfur* is the etiological agent responsible for seborrhoeic dermatitis and Pityriasis versicolor (Eichstedt's disease), while *Trycophyton rubrum* is the agent responsible for onychomycosis, athletes foot, tinea barbae (beard ringworm) and tinea corporis (body ringworm).

With the aim of identifying any potential antifungal activity in the *Syringa vulgaris* extracts, microbiological assays have been prepared, generally known as multiple dilution assays. Such assays have been performed using the following fungal strains:
*Trycophyton rubrum* ATCC 28188 and *Malassezia furfur* ST 8036.

*Syringa vulgaris* Extracts 1 and 2, verbascoside and isoverbascoside have been assayed at concentrations of 0.625 mg/ma, 1.25 mg/ml, 2.5 mg/ml and 5 mg/ml. The fungal strains used for testing have been inoculated into culture-broth (in Tryptone soy broth medium, for *Malassezia furfur* the culture medium has been supplemented with 2 ml/100 ml of olive oil) containing *Syringa vulgaris* extracts 1 and 2, verbascoside and isoverbascoside at the concentrations described above. In parallel with these tests, culture broths containing the microbial strain alone have been prepared (controls). The culture-broths have been incubated at 30° C. for a period of 28 days. Samples of the various culture-broths have been taken at 0, 7, 14, 21 and 28 days, with the aim of counting the number of CFU/ml in relation to the various fungal strains, by plating the cultures on solid medium. A certain number of serial dilutions have been prepared for each sample in order to determine the fungal load of each culture-broth. Each dilution has been assayed in triplicate on solid medium. Then number of CPUs reported in the table is the mean of the counts performed on the triplicate assays. The results obtained are reported in the following table.

TABLE 14 the effect of *Syringa vulgaris* Extracts 1 and 2 on the growth of *Trycophyton rubrum* ATCC 28188

| Samples | T0 (CFU/ml) | T7d (CFU/ml) | T14d (CFU/ml) | T21d (CFU/ml) | T28d (CFU/ml) |
|---|---|---|---|---|---|
| Control | $9.8 \times 10^4$ | $7.1 \times 10^5$ | $9.2 \times 10^5$ | $1.8 \times 10^5$ | $1.5 \times 10^5$ |
| Extract 1 (5 mg/ml) | $8.5 \times 10^4$ | <10 | <10 | <10 | <10 |
| Extract 1 (2.5 mg/ml) | $8.3 \times 10^4$ | <10 | <10 | <10 | <10 |
| Extract 1 (1.25 mg/ml) | $7.7 \times 10^4$ | <10 | <10 | <10 | <10 |
| Extract 1 (0.625 mg/ml) | $7.2 \times 10^4$ | $1.3 \times 10^3$ | $3.3 \times 10^5$ | $3.1 \times 10^5$ | $3.3 \times 10^5$ |
| Extract 2 (5 mg/ml) | $6.8 \times 10^4$ | <10 | <10 | <10 | <10 |
| Extract 2 (2.5 mg/ml) | $8 \times 10^4$ | $5.8 \times 10^2$ | $5.2 \times 10^4$ | $3.5 \times 10^4$ | $2.1 \times 10^4$ |
| Extract 2 (1.25 mg/ml) | $9 \times 10^4$ | $2.4 \times 10^3$ | $2 \times 10^5$ | $5.5 \times 10^4$ | $3.5 \times 10^4$ |
| Extract 2 (0.625 mg/ml) | $6.1 \times 10^4$ | $6.6 \times 10^3$ | $2.7 \times 10^5$ | $2.3 \times 10^5$ | $1.2 \times 10^5$ |

TABLE 15 the effect of *Syringa vulgaris* Extracts 1 and 2 on the growth of *Malassezia furfur* ST 8036

| Samples | T0 (CFU/ml) | T7d (CFU/ml) | T14d (CFU/ml) | T21d (CFU/ml) | T28d (CFU/ml) |
|---|---|---|---|---|---|
| Control | $3.9 \times 10^3$ | $1.1 \times 10^5$ | $2.7 \times 10^5$ | $3.8 \times 10^4$ | $3.6 \times 10^4$ |
| Extract 1 (5 mg/ml) | $2.7 \times 10^3$ | <10 | <10 | <10 | <10 |
| Extract 1 (2.5 mg/ml) | $2.8 \times 10^3$ | <10 | <10 | <10 | <10 |
| Estratto 1 (1.25 mg/ml) | $3.2 \times 10^3$ | <10 | <10 | <10 | <10 |
| Extract 1 (0.625 mg/ml) | $2.9 \times 10^3$ | <10 | <10 | <10 | <10 |
| Extract 2 (5 mg/ml) | $3 \times 10^3$ | <10 | <10 | <10 | <10 |
| Extract 2 (2.5 mg/ml) | $2.6 \times 10^3$ | <10 | <10 | <10 | <10 |
| Extract 2 (1.25 mg/ml) | $2.2 \times 10^3$ | <10 | <10 | <10 | <10 |
| Extract 2 (0.625 mg/ml) | $3.9 \times 10^3$ | $1.7 \times 10^4$ | $6.1 \times 10^4$ | $3.5 \times 10^4$ | $3.1 \times 10^4$ |

From the results obtained it is clear that both Extract 1 and Extract 2 display significant inhibitory activity towards the growth of the two dermatophytes assayed.

In particular, Extract 1 shows fungicidal activity towards *Trycophyton rubrum* at a concentration as low as 1.25 mg/ml, while Extract 2 displays analogous activity a concentration of 5 mg/ml.

Extract 1 displays fungicidal activity towards *Malassezia furfur* at a concentration as low as 0.625 mg/ml, while Extract 2 displays such activity at a concentration of 1.25 mg/ml.

Verbascoside and isoverbascoside exhibited an activity comparable to Extract 1.

Preferably, the verbascoside and isoverbascoside of the invention have a purity of about 99%.

With regard to their potent effect on oxidative stress, as described in examples 4, 10 and 11, the *Syringa vulgaris* extracts forming the subject of the invention are valid tools in the prevention and treatment of disease states associated with damage due to free radicals such as:

anoxia, trauma and inflammatory based diseases of the nervous system such as cerebral stroke, cerebral and spinal trauma, haemorrhagic shock, epilepsy, cerebral ischemia and ischemic spinal injury, peripheral neuropathy and cephalalgia (B. Halliwell et al, 1992); degenerative type pathologies of the nervous system also associated with ageing or autoimmune based or having inflammatory components such as amyotrophic lateral sclerosis, multiple sclerosis, Parkinson's disease, Alzheimer's disease, senile dementia and Huntington's disease (Olanow C. W. "A Radical Hypothesis for Neurodegeneration", TINS, 1993, 16(11):439-444; Dib M. Amyotrophic lateral sclerosis: progress and prospects for treatment. Drugs 2003; 63(3): 289-310);

reperfusion damage and cardiovascular diseases including angina, percutaneous transluminal coronary angioplasty (PTCA), myocardial infarction and vasculopathies (Bagchi D, Sen C K, Ray S D, Das D K, Bagchi M, Preuss H G, Vinson J A. Molecular mechanisms of cardioprotection by a novel grape seed proanthocyanidin extract, Mutat. Res. 2003 February-March; 523-524: 87-97);

atherosclerosis and muscular damage (Mertens A, Verhamme P, Bielicki J K, Phillips M C, Quarck R, Verreth W, Stengel D, Ninio E, Navab M, Mackness B, Mackness M, Holvoet P. Increased low-density lipoprotein oxidation and impaired high-density lipoprotein antioxidant defense are associated with increased macrophage homing and atherosclerosis in dyslipidemic obese mice: LCAT gene transfer decreases atherosclerosis. Circulation 2003 Apr. 1; 107(12): 1640-6.);

dismetabolic disorders such as diabetes mellitus and the neurological, vascular and ophthalmic complications thereof (Yoshida K., Hirokawa J., Tagami S., Kawakami Y., Urata Y., Kondo T. "Weakened cellular scavenging activity against oxidative stress in diabetes mellitus: regulation of glutathione synthesis and efflux" Diabetologia, 1995 February, 38(2): 201-210);

toxic disorders such as alcoholism and the neurological complications thereof besides cirrhosis of the liver (Clot P., Tabone M., Arico S., Albano E. "Monitoring oxidative damage in patients with liver cirrhosis and different daily alcohol intake" Glut., 1994 November, 35(11):1637-43);

peripheral neuropathies including toxic neuropathies (Leonetti C, Biroccio A, Gabellini C, Scarsella M, Maresca V, Flori E, Bove L, Pace A, Stoppacciaro A, Zupi G, Cognetti F, Picardo M. Alpha-tocopherol protects against cisplatin-induced toxicity without interfering with antitumour efficacy. Int. J. Cancer 2003 Mar. 20; 104(2): 243-50);

skin and mucosal disorders such as photolysis, actinic damage, skin ageing, atopy, diseases associated with karatinocyte hyperproliferation for example psoriasis, xeroderma, skin tumours (Mittal A, Elmets C A, Katiyar S K CD11b+ cells are the major source of oxidative stress in UV radiation-irradiated skin: possible role in photo-ageing and photo-carcinogenesis. Photochem. Photobiol. 2003 March; 77(3): 259-64; Pinnell S R. Cutaneous photo-damage, oxidative stress, and topical antioxidant protection. J. Am. Acad. Dermatol. 2003 January; 48(1) 1-19; Tsukahara H, Shibata R, Ohshima Y, Todoroki Y, Sato S, Ohta N, Hiraoka M, Yoshida A, Nishima S, Mayumi M. Oxidative stress and altered antioxidant defenses in children with acute exacerbation of atopic dermatitis. Life Sci. 2003 Apr. 18; 72(22): 2509-16);

dental disorders including diseases of bacterial origin, gingivitis; viral infections such as HIV (Greenspan and Aruoma, 1994 ref. cit.); Herpes Zoster, Herpes Simplex and Cytomegalovirus;

disorders of the respiratory apparatus such as cystic fibrosis, asthma, rhinitis (including allergic), "respiratory distress" and neonatal pulmonary hypertension (Fortoul T I, Valverde M, Lopez Mdel C, Lopez I, Sanchez I, Avila-Costa M R, Avila-Casado Mdel C, Mussali-Galante P, Soria E, Rojas E. Nasal cytology and genotoxic damage in nasal epithelium and leukocytes: asthmatics versus non-asthmatics. Int. Arch. Allergy Immunol. 2003 March; 130(3): 232-5);

articular disorders including rheumatoid arthritis (Lee S H, Chang D K, Goel A, Boland C R, Bugbee W, Boyle D L, Firestein G S. Microsatellite instability and suppressed DNA repair enzyme expression in rheumatoid arthritis. J. Immunol. 2003 Feb. 15; 170(4): 2214-20);

tumour pathologies; ophthalmic disorders for example cataract, retinal degeneration (Organisciak D T, Darrow R M, Barsalou L, Kutty R K, Wiggert Susceptibility retinal light damage in transgenic rats with rhodopsin imitations. Invest. Ophthalmol. Vis. Sci. 2003 February; 44(2): 486-92);

hearing apparatus damage (Shi X, Nuttall A L. Up-regulated iNOS and oxidative damage to the cochlear stria vascularis due to noise stress. Brain Res. 2003 Mar. 28; 967(1-2): 1-10);

diminished immune response (Halliwell B et al., 1992 ref. cit.; Toyokuni S. et al. "Persistent oxidative stress in cancer" FEBS Lett., 1995 Jan. 16, 358(1): 1-3; Ames B. N., Shigenaga M. K.) gastric lesions (Yajima N., Hiraishi H., Harada T., "Protection of Cultured Rat gastric cells Against Oxidant Stress by Iron Chelation" Digestive Diseases and Sciences 1995, 40(4): 879-886).

Furthermore, in relation to their potent, effectiveness against platelet aggregation as described in example 6, the Extracts of the invention, verbascoside and isoverbascoside are valid tools in the prevention and treatment of disease states associated with the formation of platelet clots and atheromatous plaques, besides finding use for the preservation and stabilisation of purified platelets. Due to the marked anti-inflammatory activities described in example 5, anti-fungal activities (described in example 13) and antibacterial activities (Didry N. Isolation and antibacterial activity of phenylpropanoid derivatives from *Ballota nigra*. J. Ethnopharmacol. 1999, 67(2): 197-202), the *Syringa vulgaris* extracts of the invention, verbascoside and isoverbascoside are valid tools in the prevention and treatment of pathological states associated with lesions of the epidermis and skin caused by burns, cuts or lesions and mechanical trauma, diabetic sores and bedsores. Furthermore, due to the aforementioned biological activities, such extracts, verbascoside and isoverbascoside may be used as promoters of the tissue repair processes in cases of mucosal and endothelial lesions and ulcers, including those of the gastrointestinal tract and vaginal mucosa.

As a result of the high chelating activity shown in example 7, the extracts, verbascoside and isoverbascoside may be used for the treatment of numerous allergy-related pathologies, both systemic and cutaneous (for example: allergic skin reaction to $Ni^{2+}$ in topical cosmetic and pharmaceutical products). Said activity may be exploited in order to protect the body from harm caused by the presence of excess heavy metals, such as iron and copper, for example following thalassemia. A combination of radical scavenging, anti-oxidant and chelating activities, may form the basis for the use of *Syringa vulgaris* extracts, verbascoside and isoverbascoside against disease processes caused by free radicals generated by the presence of excess heavy metals.

The *Syringa vulgaris* extracts, verbascoside and isoverbascoside possess high inhibitory capacity in relation to the activities of the enzymes 5 alpha reductase, both type I and type II, and lipoxygenase, as shown in example 8. This inhibitory capacity may be exploited for the treatment and prevention of hair loss in cases of androgenetic alopecia (male pattern baldness) and alopecia aereata (patchy hair loss). Furthermore, this activity may be exploited for the treatment of juvenile acne and in subjects affected by prostate diseases dependent on the activation of 5 alpha reductase.

As reported in example 9, *Syringa vulgaris* extracts, verbascoside and isoverbascoside demonstrate high inhibitory activity in relation to the enzyme tyrosinase. This activity may be exploited in order to bring about bleaching effects on the skin.

As shown in example 13, total extracts, verbascoside and isoverbascoside display fungicidal activity in relation to two dermatophytic strains: *Tricophyton rubrum* and *Malassezia furfur*. This characteristic permits the use of such products in the topical treatment of dermatitis, particularly seborrhoeic dermatitis, onychomycosis, Pityriasis versicolor (Eichstedt's disease), athletes foot, tined barbae (beard ringworm) and, tinea corporis (body ringworm).

The doses, times and routes of administration of the treatment will be selected on the basis of the type, stage, severity and location of manifestation of the pathology. For all the pathologies mentioned, systemic and oral administration are indicated, but additionally also topical and transdermal, and in any case so as to make the active ingredient maximally available. For the oral formulations, administration in the form of tablets, lozenges and capsules, but also powders and suspensions are preferred: for topical treatment, gels, creams, ointments and solutions compatible with dermal and mucosal use are preferred, in addition to eye washes for administration into the conjunctival sac. The injectable forms are formulated using solvents for pharmaceutical use, compatible with intravenous, intramuscular and subcutaneous administration.

The therapeutic dose varies, depending on the patients age, weight, sex and type of pathology, between 0.1 mg and 2 g per day and preferably between 5 and 150 mg per day, taken in a single dose or in 2-4 doses or in slow release form, depending on the patients therapeutic need, and for periods of time varying between 1 and 120 days.

At appropriate concentrations, the same extracts, verbascoside and isoverbascoside may be formulated in the form of supplements, to be taken orally for prevention, or as aids in the treatment of changes resulting from disreactive states in humans or in veterinary medicine. Total extracts, verbascoside and isoverbascoside active at the appropriate concentrations, and in appropriate formulations, may be likewise used in cosmetics and trichological treatments.

Thanks to the absorbance spectrum of the phenylpropanoids, which ranges from 240 nm to 350 nm (UVB absorption range), such substances may be used for the preparation of sun filters.

Some examples of pharmaceutical, cosmetic and supplement preparations are reported in the following, for the purposes of non-limiting illustration:

Example 1

Capsules for Oral Use

Active ingredient: Extract titrated in verbascoside as 500 mg.
Excipients: Carbowax 6000, gelatin, distilled water, E172, Titanium dioxide Example 2

Active ingredient: Extract titrated in verbascoside as 10 mg
Excipients: pH 7 buffered injectable solution, sufficient for 2 ml Example 3

0.2% Emulsion for Topical Application

Active ingredient: Extract titrated in verbascoside as 200 mg
Excipients: Synthetic glycerides, anionic emulsifying wax, anhydrous lanolin, polysorbate 80, dimethylpolyoxane 100, dimethylpolyoxane 500, methyl-p-hydroxybenzoate, propyl-p-hydroxybenzoate, lemon essence, sufficient water to make up to 100 g
Example of an Oral Preparation:
Extract: 10 mg
Magnesium, Selenium, Folic acid, Mannitol, sodium saccharin, citric acid, lemon flavouring.

The *Syringa vulgaris* extracts, verbascoside and isoverbascoside may be formulated for use in the veterinary sector and as dietary supplements for zootechnical use, such as, as a non-limiting example; for the raising of fowl and fish.

From the above description, it is clear that the extracts for use in the preparation of drugs, cosmetics or nutritional substances advantageously allow the provision of compounds capable of having unexpectedly greater antioxidant activity, in some cases, with respect to any individual phenylpropanoid.

In addition, said extracts, verbascoside and isoverbascoside may be advantageously used as wound healing agents.

Obviously, one skilled in the art, with the aim of satisfying contingent and specific needs, can bring about a number of modifications and variations to the plant cell extract for the uses outlined above, all however contained within the scope of the invention as defined in the following claims.

We claim:
1. A method of treating one of juvenile acne, diseases of the prostate, and hair loss in a human or animal subject, the method comprising:
orally administering an effective amount of verbascoside and/or isoverbascoside to induce anti-lipoxygenase and/or anti-5-alpha reductase action in the subject, wherein the administered effective amount is between 0.1 mg and 2 g per day for a period of time between 1 and 120 days.
2. A method of using an extract prepared from a plant cell line belonging to the Oleaceae family, wherein said preparation comprises the following steps in sequence:
a) subjecting a biomass obtained following culture of said plant cell line to an enzyme deactivating treatment;
b) homogenizing the product resulting from step a);
c) separating the liquid phase of the homogenized product from cell residues by means of gravity filtration, pressure filtration or centrifugation;
d) performing an extraction of the liquid phase obtained in step c) with a hydrophobic interaction resin; and
e) recovering an extract of absorbed substances from the resin in step d) by means of elution with a mixture of alcohols having up to 6 carbon atoms in water in percentages varying from 30% up to just under 100% by volume,
said method comprising using the extract for medicine, nutrition or cosmetics, wherein said extract is used between 0.1 mg and 2 g per day for periods of time varying between 1 and 120 days and has at least one of the following properties:
anti-alpha-reductase and anti-lipoxygenase activities for the treatment of juvenile acne, diseases of the prostate, and hair loss in a human; and
said extract being orally administered in an effective amount for treating subjects suffering from juvenile acne, diseases of the prostate, and hair loss in a human.
3. The method of using the extract prepared according to claim 2, further comprising the step of formulating the extract to be administered into a medication.
4. The method according to claim 2, wherein the extract is administered in doses of between 0.1 and 100 mg/kg body weight for 1-100 days.
5. The method according to claim 3, comprising a treatment wherein the doses of extract per treatment cycle are between 0.1 and 100 mg/kg for 1-100 days.

* * * * *